United States Patent [19]

Gerber et al.

[11] Patent Number: 5,700,487

[45] Date of Patent: Dec. 23, 1997

US005700487A

[54] TREATMENT OF PULMONARY INFLAMMATION

[75] Inventors: Nicholas Gerber, Worthington; Glen Apseloff; Daniel L Mullet, both of Columbus, all of Ohio

[73] Assignee: The Ohio State University, Columbus, Ohio

[21] Appl. No.: 610,271

[22] Filed: Mar. 4, 1996

[51] Int. Cl.[6] .................. A61K 33/24; A61K 31/28
[52] U.S. Cl. ............................. 424/650; 514/492
[58] Field of Search ..................... 424/650; 514/492

[56] References Cited

U.S. PATENT DOCUMENTS

| | | |
|---|---|---|
| 4,044,126 | 8/1977 | Cook et al. . |
| 4,364,923 | 12/1982 | Cook et al. . |
| 4,708,964 | 11/1987 | Allen ........................ 514/533 |
| 4,745,127 | 5/1988 | Atkinson et al. . |
| 5,175,006 | 12/1992 | Matkovic et al. ................ 424/650 |
| 5,350,744 | 9/1994 | Girard et al. . |

*Primary Examiner*—Raymond Henley, III
*Attorney, Agent, or Firm*—Fay, Sharpe, Beall, Fagan, Minnich & McKee

[57] ABSTRACT

A method of treating pulmonary inflammation in mammals, comprising administering an effective amount of a pharmaceutically acceptable gallium compound and wherein said gallium is elected from the group consisting of gallium nitrate, gallium citrate, gallium chloride, gallium carbonate, gallium acetate, gallium tartrate, gallium oxalate, gallium oxide, gallium arsenide and hydrated gallium oxide.

7 Claims, No Drawings

TREATMENT OF PULMONARY INFLAMMATION

BACKGROUND OF THE INVENTION

This invention relates to a method of treating pulmonary inflammation. More particularly, this invention relates to a method of preventing and alleviating pulmonary inflammation via the administration of a gallium containing compound.

The inventive method is particularly well suited to be used in the treatment of asthma. Throughout the specification, numerous references will be made to use of the treatment in the prevention and/or alleviation of inflammation associated with the disease asthma. However, it should be realized that the inventive method could be used in the treatment of pulmonary inflammation resulting from any cause.

DESCRIPTION OF THE ART

Pulmonary inflammation, such as the type typically associated with the disease asthma, is characterized by an increased responsiveness of the trachea and bronchi to various stimuli and manifested by a widespread airway narrowing causing episodic dyspnea, coughing and wheezing and the associated debilitation of the afflicted person. In fact, in severe cases, pulmonary inflammation can result in death.

The primary contributor to the symptoms of asthma is the inflammation of the trachea and bronchial air passages. Accordingly, treatment for asthma has typically included the administration of aerosol formulations including anti-inflammatory steroids. Particularly, it has been found effective to spray anti-inflammatory cortical steroids into the bronchial system prophylactically. For example, U.S. Pat. No. 4,044,126, herein incorporated by reference, discloses a process including the delivery of an anti-inflammatory steroid. Similarly, U.S. Pat. No. 5,350,744, is directed to the administration of a leukotriene biosynthesis inhibitor as an anti-asthmatic agent. More particularly, the patent is directed to the use of phenylnaphthalene lactones as inhibitors of leukotriene biosynthesis.

Accordingly, the use of steroidal and hormone-derived compounds in prevention of pulmonary inflammation associated with asthma, has found general acceptance in the art. However, problems are presented by the use of these compounds such as adrenal insufficiency (which has resulted in fatally's) and increased risk of infections.

Therefore, a search for an alternate treatment for pulmonary disease has continued.

SUMMARY OF THE INVENTION

It is a primary object of this invention to provide a new and improved method for the treatment of pulmonary inflammation.

It is an advantage of this invention to provide a new and improved method that is effective in preventing and reducing pulmonary inflammation.

A still further advantage of this invention is that a pharmaceutically acceptable compound is utilized to prevent and reduce pulmonary inflammation.

Yet another advantage of this invention is the ability of the process to prevent onset of asthmatic attacks and to reduce symptoms subsequent to its initiation.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the method of this invention comprises the administration of an effective amount of a pharmaceutically acceptable compound containing gallium to prevent the onset of pulmonary inflammation and/or to reduce the affects of pulmonary inflammation. The method is particularly effective in preventing asthmatic attacks and in mitigating the effects thereof once a patient is afflicted. In this regard, the method is believed particularly suited to use in mammals susceptible to pulmonary inflammation associated with asthma.

In a particularly preferred embodiment, the gallium is administered in the form of pharmaceutically acceptable compound selected from the group consisting of gallium nitrate, gallium citrate, gallium chloride, gallium carbonate, gallium acetate, gallium tartrate, gallium oxalate, gallium oxide, hydrated gallium oxide, gallium arsenide and mixtures thereof. Within this group, gallium nitrate is a particularly preferred compound for the inventive treatment. Preferably, the gallium compound is administered orally, intravenously, subcutaneously, intramuscularly, or through inhalation.

DETAILED DESCRIPTION OF THE INVENTION

As described above, it is believed that asthma and other pulmonary diseases, allergic reactions and physical trauma to pulmonary tissue are problematic to a patient because the pulmonary tissues experience pathological loss of function from vasoconstriction followed by vasodilation, stasis, hyperemia, accumulation of leukocytes, and exudation of fluid causing swelling and air passage constriction. In general, this series of events is believed largely caused by the significant regional increase in leucocytes concentration. Accordingly, it is a patient's own autoimmune response which is believed to result in the debilitating and potentially life-threatening pulmonary inflammation.

Applicants have found that gallium has a unique biochemical and clinical ability suited to suppression of the autoimmune system involved in pulmonary inflammation.

Reference will now be made in detail to the present preferred embodiment of the invention, examples of which are illustrated by the following experiments. While the inventive process will be described in connection with the procedure, it will be understood that it is not intended to limit the invention to that procedure or examples. On the contrary, it is intended to cover all alternatives, modifications and equivalents which may be included within the spirit and scope of the invention defined by the appended claims.

EXAMPLES

The effectiveness of gallium in preventing and/or reducing pulmonary inflammation, was evaluated in 30 male B6D2F1/J mice (weighing between 21.9–28.3 grams). The mice were randomly divided into three groups of ten mice and prepared as follows:

Group I diseased and treated with a vehicle;
Group II diseased and treated with gallium;

Group III healthy and treated with a vehicle.

In each of the Groups, pulmonary inflammation was induced by intraperitoneal injection of 0.5 ml normal saline containing 8 ug ovalbumin (OVA) and 2 ug Al(OH)$_3$ gel on days 0 and 5 of the experiment. On day 12, the mice of Groups I and II were exposed to 1% aerosolized OVA for one hour in both the morning and afternoon.

The methodology of inducing the pulmonary inflammation is more particularly set forth in the article entitled "Characterization of a Murine Model of Allergic Pulmonary Inflammation", Int. Arch. Allergy Immunol. 1994: 105: 83–90, Kung, et al., herein incorporated by reference.

All mice were injected subcutaneously with either gallium nitrate (45 mg/kg elementel Ga, 28.75 mg/ml/trisodium citrate dihydrate and sodium hydroxide—when necessary—to adjust the pH to a range of 6.0 to 7.0) or an equivalent volume of vehicle (citrate solution, 6.6024 ml/kg) on day 11 and were euthanized with pentobarbital and ether on day 14.

Bronchoalveolar lavage (BAL) revealed eosinophils, an indication of an allergic reaction and a hallmark of the disease, and histology for three groups revealed perivascular/peribronchiolar granulocytic infiltrate (0 equals none, 1 equals minimal, 2 equals mild, 3 equals moderate, 4 equals marked). The results for each analysis are set forth in the following table.

TABLE

| Sample | I citrate grp | II gallium grp | III control |
|---|---|---|---|
| Mean eosinophils level | 47.4 | 23.5 | 1 |
| Sample Size | 10 | 10 | 9 |
| SD | 31.956 | 21.722 | 1.000 |
| SEM | 10.105 | 6.869 | 0.3333 |
| Median | 43.500 | 15.000 | 1.000 |
| Lower 95% CI | 24.542 | 7.962 | 0.2313 |
| Upper 95% CI | 70.258 | 39.038 | 1.769 |
| Minimum | 1.000 | 4.000 | 0.000 |
| Maximum | 85.000 | 73.000 | 3.000 |
| Mean infiltrate level | 2.2 | 1.8 | 0 |
| SD | 1.033 | 0.4216 | 0.000 |
| SEM | 0.3266 | 0.1333 | 0.000 |
| Median | 2.500 | 2.000 | 0.000 |
| Lower 95% CI | 1.461 | 1.498 | 0.000 |
| Upper 95 CI | 2.939 | 2.102 | 0.000 |
| Minimum | 0.000 | 1.000 | 0.000 |
| Maximum | 3.000 | 2.000 | 0.000 |

The differences in BAL between Groups I and II were significant (P<0.05), and the histological evaluation supported the findings, i.e. the efficacy of gallium on pulmonary inflammation.

Accordingly, it is theorized that the effectiveness of gallium in autoimmune suppression results in a decrease in leukocyte levels in traumatized pulmonary tissue and effectively prevents the constriction thereof.

Thus, it is apparent that there has been provided, in accordance with the invention, a method that fully satisfies the objects, aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications and variations as they fall within the spirit and broad scope of the appended claims.

What is claimed:

1. A method of treating pulmonary inflammation in mammals, comprising administering an effective amount of a pharmaceutically acceptable gallium compound selected from the group consisting of gallium nitrate, gallium citrate, gallium chloride, gallium carbonate, gallium acetate, gallium tartrate, gallium oxalate, gallium oxide, gallium arsenide, and hydrated gallium oxide.

2. The method of claim 1 wherein said gallium compound is gallium nitrate.

3. The method of claim 1 wherein said gallium compound is administered orally, intravenously, subcutaneously, intramuscularly, or through inhalation.

4. The method of claim 1 wherein said gallium compound is administered prophylactically prior to the onset of said pulmonary inflammation.

5. The method of claim 1 wherein said gallium compound is administered after the onset of said pulmonary inflammation.

6. The method of claim 1 wherein said mammal is a human.

7. The method of claim 1 wherein said pulmonary inflammation is associated with the disease asthma.

* * * * *